US007462446B2

(12) United States Patent
Zhang et al.

(10) Patent No.: US 7,462,446 B2
(45) Date of Patent: Dec. 9, 2008

(54) MAGNETIC NANOPARTICLE COMPOSITIONS AND METHODS

(75) Inventors: Miqin Zhang, Bothell, WA (US); Nathan Kohler, Providence, RI (US); Jonathan Whitney Gunn, Seattle, WA (US)

(73) Assignee: University of Washington, Seattle, WA (US)

(*) Notice: Subject to any disclaimer, the term of this patent is extended or adjusted under 35 U.S.C. 154(b) by 59 days.

(21) Appl. No.: 11/386,053

(22) Filed: Mar. 20, 2006

(65) Prior Publication Data

US 2006/0216239 A1 Sep. 28, 2006

Related U.S. Application Data

(60) Provisional application No. 60/663,158, filed on Mar. 18, 2005.

(51) Int. Cl.
*C12Q 1/70* (2006.01)
*C12Q 1/68* (2006.01)

(52) U.S. Cl. .............................................. 435/5; 435/6

(58) Field of Classification Search ................ 424/9.32, 424/486; 435/5, 6

See application file for complete search history.

(56) References Cited

U.S. PATENT DOCUMENTS

| | | | | |
|---|---|---|---|---|
| 6,130,101 | A | 10/2000 | Mao et al. | |
| 6,514,481 | B1 * | 2/2003 | Prasad et al. | 424/9.32 |
| 6,767,635 | B1 | 7/2004 | Bahr et al. | |
| 6,972,326 | B2 | 12/2005 | Haugland et al. | |
| 2003/0201208 | A1 * | 10/2003 | Koch et al. | 209/39 |
| 2004/0101822 | A1 * | 5/2004 | Wiesner et al. | 435/6 |

OTHER PUBLICATIONS

M.D. Butterworht, L. LLLum and S.S. Davis, Preparatiion of ultrafine silica- and PEG-coated magnetic particles, Colloids and Surface A: Physiochemical and Engineering Aspects, 179, 93-102, 2001.*

Butterworth, M.D., et al., "Preparation of Ultrafine Silica- and PEG-Coated Magnetite Particles," *Colloids and Surfaces A: Physicochemical and Engineering Aspects 179*:93-102, 2001.

Kohler, N., et al., "A Bifunctional Poly(ethylene glycol) Silane Immobilized on Metallic Oxide-Based Nanoparticles for Conjugation With Cell Targeting Agents," *Journal of the American Chemical Society 126*(23):7206-7211, 2004.

Sun, S., and H. Zeng, "Size-Controlled Synthesis of Magnetite Nanoparticles," *Journal of the American Chemical Society 124*(28):8204-8205, 2002.

Zhang, Y., et al., "Surface Modification of Superparamagnetic Magnetite Nanoparticles and Their Intracellular Uptake," *Biomaterials 23*:1553-1561, 2002.

* cited by examiner

*Primary Examiner*—Michael G. Hartley
*Assistant Examiner*—Jagadishwar R Samala
(74) *Attorney, Agent, or Firm*—Christensen O'Connor; Johnson Kindness PLLC

(57) ABSTRACT

A nanoparticle having a core comprising a magnetic material and surface to which are covalently coupled a plurality of silane moieties, wherein each silane moiety comprises a polyalkylene oxide moiety. The nanoparticle can further include a targeting agent, a targeting agent and a diagnostic agent, or a targeting agent and a therapeutic agent. Methods for using the nanoparticle to detect and treat tissues of interest.

7 Claims, 7 Drawing Sheets

MAGNETIC NANOPARTICLE COMPOSITIONS AND METHODS

CROSS-REFERENCES TO RELATED APPLICATION

The present application claims the benefit of U.S. patent application No. 60/663,158, filed Mar. 18, 2005, incorporated herein by reference in its entirety.

STATEMENT OF GOVERNMENT LICENSE RIGHTS

This invention was made with government support under Grant No. N01-C037122 and Grant No. R01CA119408 awarded by the National Institutes of Health. The government has certain rights in the invention.

BACKGROUND OF THE INVENTION

Magnetic resonance imaging (MRI) is an appealing non-invasive approach for early cancer diagnostics and therapeutics. While the imaging capabilities of these instruments have revolutionized imaging technology, the resolution of the instrument is limited to the elucidations of lesions within the body on the order of 1 mm. This limitation of the instrument has led to the development of several types of contrast enhancement agents including magnetite/dextran-based nanoparticles and chelated gadolinium contrast agents, which are currently available on the market and used widely in clinical applications. However, gadolinium (Gd) complex contrast agents are effective only when present in millimolar concentrations. Because of the superparamagnetic property, iron oxide nanoparticles have been found effective in nanomolar concentrations and can better serve as contrast enhancement agents for MRI. Apart from serving as contrast enhancement agents, superparamagnetic nanoparticles can be used as drug carriers for controlled drug release; they can accumulate in tumors very efficiently through enhanced permeation and retention.

However, when nanoparticles are conjugated with target agents or undergo any surface modification, particle agglomeration as a result of their large surface-to-volume ratio becomes a primary concern. When nanoparticles agglomerate, they not only lose their intended functionality, but can also be quickly cleared by macrophages or accumulated in the reticule-endothelial system before they can reach the target cells.

One approach to solving this problem is to modify the particulate surface with poly(ethylene glycol) (PEG) self-assembled monolayers. Surfaces covered with PEG have proven to be nonimmunogenic, nonantigenic, and protein resistant. While the PEG moiety provides an efficient system to increase particulate circulation time in blood, the nanoparticle systems must also be coupled with tumor targeting agents to be useful for the intended applications. Thus, the PEG moiety immobilized on nanoparticles must also provide an active functional group capable of conjugating with targeting agents.

PEG is used widely to functionalize proteins and peptides for drug delivery. Research in cell targeting has also utilized functional PEG molecules conjugated with folic acid on liposomes. Monofunctional PEG molecules coupled to proteins are known to prolong the particle circulation time in blood and reduce immunogenicity. While functionalized carboxyl or amine PEGs are widely available, they remain expensive and require chemical modification to convert to their corresponding silanes. Further, these functional PEGs are available mainly in high molecular weights, which may inhibit PEG monolayer self-assembly on the nanoparticle surface due to the labile nature of PEG molecules. Currently available PEGs can conjugate with only one type of functional group present in targeting agents, typically either amine or carboxyl groups, and, in most of cases, they are not suitable for nanoscaled devices such as nanoparticle systems due to their high molecule weight. PEG silylation normally occur in organic solution, whereas conjugation with tumor targeting agents such as folic acid or antibodies needs to be conducted in aqueous solution. Thus, PEG self-assembled monolayers (SAM) must be flexible enough to prevent agglomeration during solvent exchange and remain active in solvents to provide a terminus for conjugation.

Despite the advances in the use of nanoparticles as contrast agents and drug carriers noted above, a need exists for nanoparticles that can be surface-modified to function as both contrast enhancement agents and drug carriers simultaneously, allowing real-time monitoring of tumor response to drug treatment. The present invention seeks to fulfill this need and provides further related advantages.

SUMMARY OF THE INVENTION

In one aspect, the invention provides a compound having the formula:

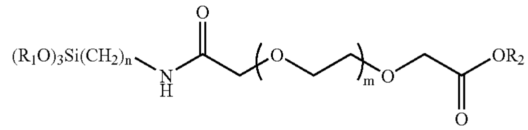

wherein, $R_1$ is selected from the group consisting of alkyl and aryl;

$R_2$ is selected from the group consisting of alkyl and aryl;

n is 1, 2, 3, 4, 5, or6; and m is an integer from about 10 to about 1000.

In another aspect, the invention provides a particle comprising:

(a) a core having a surface; and (b) a plurality of silane moieties, wherein the silane moiety is covalently coupled to the surface, and wherein the silane moiety has the formula:

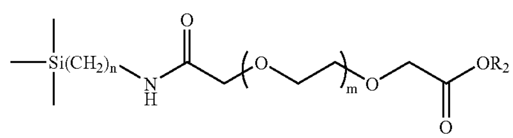

wherein, $R_2$ is selected from the group consisting of alkyl and aryl;

n is 1, 2, 3, 4, 5, or 6; and m is an integer from about 10 to about 1000.

In one embodiment, the particle is a magnetic nanoparticle comprising:

(a) a core comprising a magnetic material and having a surface; and (b) a plurality of silane moieties, wherein each silane moiety is covalently coupled to the surface, and wherein the silane moiety has the formula:

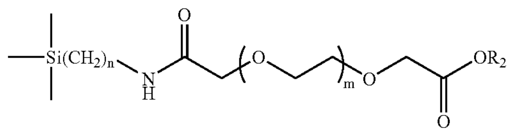

wherein, $R_2$ is selected from the group consisting of alkyl and aryl;

n is 1, 2, 3, 4, 5, or 6; and m is an integer from about 10 to about 1000.

In one embodiment, the magnetic nanoparticle further includes a targeting moiety that is effective to direct the nanoparticle to a specific site where the nanoparticle is bound. The nanoparticle comprises:

(a) a core comprising a magnetic material and having a surface; and (b) a plurality of silane moieties, wherein each silane moiety is covalently coupled to the surface, wherein at least a portion of the plurality of silane moieties comprises a targeting agent, and wherein the silane moieties comprise a polyalkylene oxide moiety intermediate the surface and the targeting agent.

In one embodiment, the magnetic nanoparticle including the targeting moiety comprises:

(a) a core comprising a magnetic material and having a surface; and (b) a plurality of silane moieties, wherein each silane moiety is covalently coupled to the core, and wherein the silane moiety has the formula:

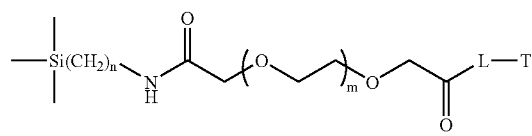

wherein, n is 1, 2, 3, 4, 5, or 6;

m is an integer from about 10 to about 1000;

L is a direct bond or a linker; and

T is a targeting agent.

In another aspect of the invention, compositions that include the particles of the invention are provided. In one embodiment, the composition includes a nanoparticle suitable for administration to a human.

In other aspects, the invention provides methods for using nanoparticles.

In one embodiment, methods for detecting cells or tissues by magnetic resonance imaging using the nanoparticles are provided. In one embodiment, the method includes the steps of:

(a) contacting cells or tissues of interest with a nanoparticle having affinity and specificity for the cells or tissues of interest, wherein the nanoparticle comprises:

(i) a core comprising a magnetic material and having a surface, and (ii) a plurality of silane moieties, wherein each silane moiety is covalently coupled to the surface, wherein the silane moiety comprises a targeting moiety having affinity and specificity to the cells or tissues of interest, and wherein the silane moiety comprises a polyalkylene oxide moiety intermediate the core and the targeting agent; and (b) measuring the level of binding of the nanoparticle, wherein an elevated level of binding, relative to normal cells or tissues, is indicative of binding to the cells or tissues of interest.

In another embodiment, methods for treating a tissue using the nanoparticles are provided. In one embodiment, the method includes contacting a tissue of interest with a nanoparticle having affinity and specificity for the tissue of interest, wherein the nanoparticle comprises:

(a) a core comprising a magnetic material and having a surface, and (b) a plurality of silane moieties, wherein each silane moiety is covalently coupled to the surface, wherein at least a portion of the plurality of silane moieties comprise a targeting moiety having affinity and specificity to the tissue of interest, wherein at least a portion of the plurality of silane moieties comprise a therapeutic agent, wherein each silane moiety comprising a targeting agent comprises a polyalkylene oxide moiety intermediate the core and the targeting agent; and wherein each silane moiety comprising a therapeutic agent comprises a polyalkylene oxide moiety intermediate the core and the therapeutic agent.

Methods for making the silane compound and labeled particles are also provided.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
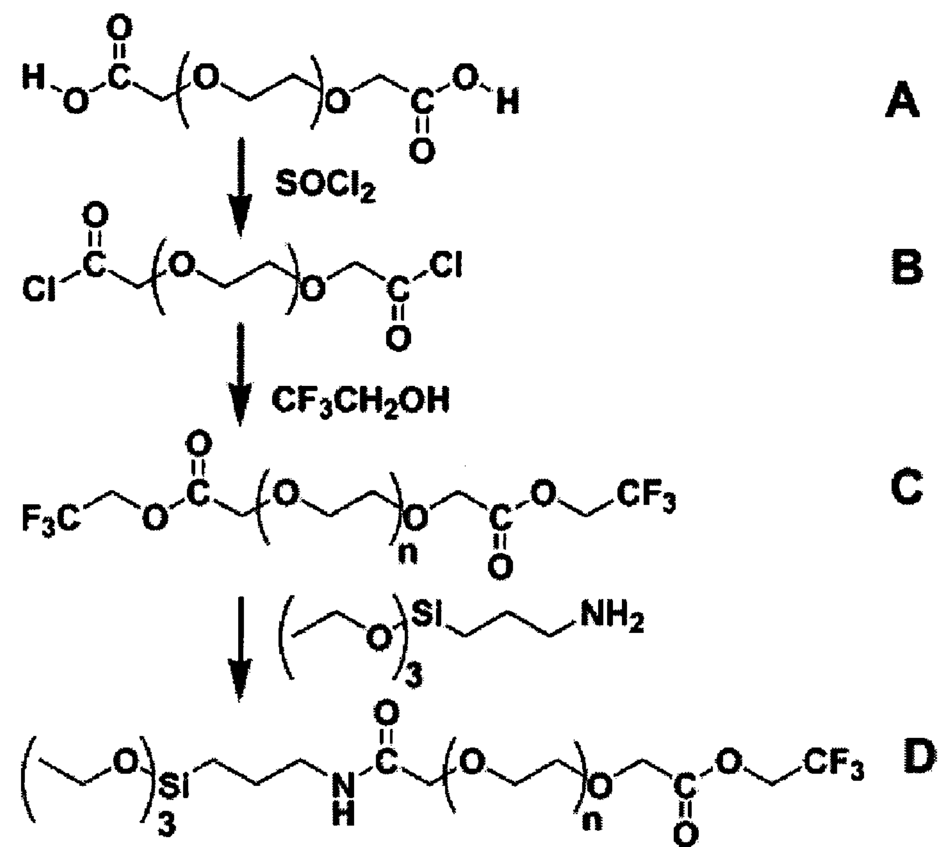
FIG. 1 is a schematic illustration of the synthesis of a trifluoroethylester-terminal PEG silane, a representative silane of the present invention.

The present invention provides a silane compound useful in labeling particles to render the particles further reactive toward one or more targeting, therapeutic, or diagnostic agents to provide functional particle conjugates; particles labeled with the silane compound that are further reactive toward one or more targeting, therapeutic, or diagnostic agents to provide particle conjugates; particle conjugates including one or more targeting, therapeutic, or diagnostic agents; and methods for using the particle conjugates to detect, image, and treat cells and tissues.

In one aspect, the invention provides a compound having the formula:

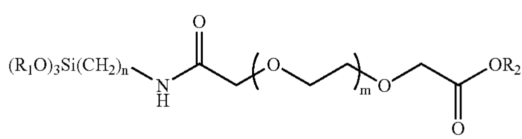

wherein, $R_1$ is selected from the group consisting of alkyl and aryl;

$R_2$ is selected from the group consisting of alkyl and aryl;

n is 1, 2, 3, 4, 5, or 6; and m is an integer from about 10 to about 1000.

Suitable alkyl groups for $R_1$ and $R_2$ include substituted and unsubstituted $C_1$-$C_6$ straight chain or branched alkyl groups. In one embodiment, $R_1$ is ethyl. In one embodiment, $R_2$ is 2,2,2-trifluoroethyl.

Suitable aryl groups for $R_1$ and $R_2$ include substituted and unsubstituted $C_6$-$C_{12}$ aryl groups.

In the compound, the number of methylene groups (n) can vary from 1 to 6. In one embodiment, n is 3.

The compound includes a poly(oxyethylene) group having oxyethylene repeating units (m). As noted above, m is an integer from about 10 to about 1000 (i.e., polyethylene glycol having molecular weight of from about 500 to about 50,000 g/mole). In one embodiment, m is from about 10 to about 20. In one embodiment, m is about 10.

The silane compounds of the invention are useful in labeling particles (e.g., nanoparticles, magnetic particles, superparamagnetic particles) to render the particles further reactive toward one or more targeting, therapeutic, or diagnostic agents to provide functional particle conjugates.

In another aspect, the invention provides a particle comprising:

(a) a core having a surface; and (b) a plurality of silane moieties, wherein the silane moiety is covalently coupled to the surface, and wherein the silane moiety has the formula:

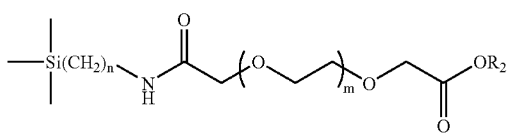

wherein, $R_2$ is selected from the group consisting of alkyl and aryl;

n is 1, 2, 3, 4, 5, or 6; and m is an integer from about 10 to about 1000.

For the particles of the invention prepared from the silane compounds described herein, n, m, and $R_2$ are as described for the silane compounds.

The particle includes a core having a surface that can be reacted with the silane compounds of the invention. The particles can be core-shell particles in which the core is a material different from the shell. In one embodiment, the surface or shell comprises hydroxyl groups that are reactive toward the silane compounds.

In certain embodiments, the core includes a magnetic material. Suitable magnetic materials include metal oxides, such as ferrous oxide, ferric oxide, silicon oxide, polycrystalline silicon oxide, aluminum oxide, germanium oxide, zinc selenide, tin dioxide, titanium dioxide, indium tin oxide, and gadolinium oxide. Mixtures of one or more metal oxide can be used.

In addition to magnetic materials, the core can include non-magnetic materials, such as silicon nitride, stainless steel, titanium, and nickel titanium. Mixtures of one or more non-magnetic materials can also be used.

The particles of the invention can be nanoparticles having particle diameter of from about 2 nm to about 200 nm.

The particles of the invention include a plurality of silane moieties covalently coupled to the core's surface. In one embodiment, the covalently coupled silane moieties provide a layer surrounding the core. In one embodiment, the covalently coupled silane moieties provide a monolayer on the core's surface.

In one embodiment, the particle is a magnetic nanoparticle comprising:

(a) a core comprising a magnetic material and having a surface; and (b) a plurality of silane moieties, wherein each silane moiety is covalently coupled to the surface, and wherein the silane moiety has the formula:

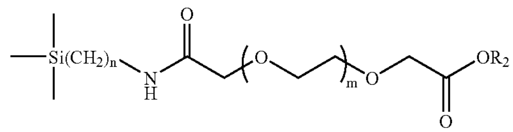

wherein, $R_2$ is selected from the group consisting of alkyl and aryl;

n is 1, 2, 3, 4, 5, or 6; and m is an integer from about 10 to about 1000.

For these particles, the core has a surface and includes the materials described above. By virtue of $R_2$ these particle is a reactive toward and ready for covalent coupling to a targeting, diagnostic, or therapeutic agent.

In one embodiment, the magnetic nanoparticle further includes a targeting moiety that is effective to direct the nanoparticle to a specific site where the nanoparticle is bound. The nanoparticle comprises:

(a) a core comprising a magnetic material and having a surface; and (b) a plurality of silane moieties, wherein each silane moiety is covalently coupled to the surface, wherein at least a portion of the plurality of silane moieties comprises a targeting agent, and wherein the silane moieties comprise a polyalkylene oxide moiety intermediate the surface and the targeting agent.

Suitable targeting agents include agents that are effective in directing the nanoparticle to a specific site (e.g., cells or tissues in vivo or in vitro) and that result in binding of the nanoparticle to the site.

Representative targeting agents include peptide, proteins, ligands, nucleic acids, and nucleus targeting molecules, among others.

Representative peptide targeting agents include, for example, chlorotoxin, RGD (arginine-glycine-aspartic acid), and Tat peptide.

Representative protein targeting agents include, for example, annexins such as annexin V, MHC II, and epidermal growth factor.

Representative ligand targeting agents include small molecules, for example, folic acid and methotrexate.

Representative nucleus targeting agents include, for example, histone, Tat nuclear targeting sequence (GRKKRRORRRAP), and platelet-derived growth-factor-related molecules.

Other targeting agents include targeting agents using phage display.

The nanoparticle including the targeting agent can further include other useful agents. Other useful agents include diagnostic agents and therapeutic agents.

Suitable diagnostic agents include agents that provide for the detection of the nanoparticle by methods other than magnetic resonance imaging.

Suitable diagnostic agents include light-emitting compounds (e.g., fluorophores, phosphors, and luminophors). Suitable fluorophores include fluorophores that can be covalently coupled to silane moiety and that emit fluorescence in the visible and near-infrared region of the spectrum. Representative fluorophores include ALEXA FLUORS (sulfonated xanthene derivatives, see U.S. Pat. No. 6,130,101, expressly incorporated herein by reference in its entirety), AMCA, BODIPYs (dipyrrometheneboron difluoride derivatives, see U.S. Pat. No. 6,972,326, expressly incorporated herein by reference in its entirety), CASCADE BLUE, CASCADE YELLOW, coumarins, fluoresceins, eosins, erythrosins, rhodamines, OREGON GREEN, PACIFIC BLUE, and TEXAS RED dyes commercially available in suitable reactive forms from Molecular Probes, Inc. (849 Pitchford Avenue, Eugene, Oreg.) and cyanine dyes (e.g., Cy2, Cy3, Cy3B, Cy3.5, Cy5, Cy5.5, and Cy7) CYDYE fluors commercially available in suitable reactive forms from Amersham Pharmacia Biotech (Piscataway, N.J., now GE Healthcare).

Other suitable diagnostic agents include radiolabels (e.g., radio isotopically labeled compounds) such as $^{125}I$, $^{14}C$, and $^{31}P$, among others.

In embodiments that include a targeting agent and a diagnostic agent, a portion of the plurality of silane moieties comprise a diagnostic agent (e.g., a fluorescent agent or fluorophore, a radiolabel).

Suitable therapeutic agents include cytotoxic agents. Representative therapeutic agents include chemotherapeutic agents such as methotrexate, docetaxel, cisplatin, and etoposide, among others. Other therapeutic agents include nucleic acid molecules (e.g., DNAs and RNAs, such as siRNAs) for specific cancers and diseases.

In embodiments that include a targeting agent and a therapeutic agent, a portion of the plurality of silane moieties comprise a therapeutic agent (e.g., a cytotoxic agent, chemotherapeutic agent).

In certain embodiment, the nanoparticle includes a targeting agent, one or more diagnostic agents, and one or more therapeutic agents.

In one embodiment, the magnetic nanoparticle including the targeting moiety comprises:

(a) a core comprising a magnetic material and having a surface; and (b) a plurality of silane moieties, wherein each silane moiety is covalently coupled to the core, and wherein the silane moiety has the formula:

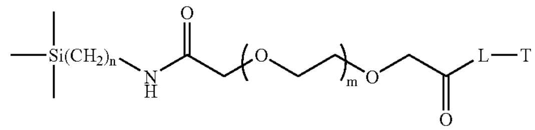

wherein, n is 1, 2, 3, 4, 5, or 6;

m is an integer from about 10 to about 1000;

L is a direct bond or a linker; and

T is a targeting agent.

For this embodiment, the linker may be one or more atoms that link the targeting agent to the polyoxyethylene moiety covalently coupled to the core surface. The targeting moiety can be as described above.

In another aspect of the invention, compositions that include the particles of the invention are provided. In one embodiment, the composition includes a nanoparticle suitable for administration to a human or an animal subject, wherein the nanoparticle comprises:

(a) a core comprising a magnetic material and having a surface; and (b) a plurality of silane moieties, wherein each silane moiety is covalently coupled to the surface, wherein at least a portion of the plurality of silane moieties comprise a targeting moiety, and wherein the silane moieties comprise a polyalkylene oxide moiety intermediate the surface and the targeting agent.

The composition can include an acceptable carrier. In one embodiment, the composition is a pharmaceutically acceptable composition and includes a pharmaceutically acceptable carrier. As used herein the term "carrier" refers to a diluent (e.g., saline) to facilitate the delivery of the particles.

In other aspects, the invention provides methods for using nanoparticles.

In one embodiment, methods for detecting cells or tissues by magnetic resonance imaging using the nanoparticles are provided. In one embodiment, the method includes the steps of:

(a) contacting cells or tissues of interest with a nanoparticle having affinity and specificity for the cells or tissues of interest, wherein the nanoparticle comprises:

(i) a core comprising a magnetic material and having a surface, and (ii) a plurality of silane moieties, wherein each silane moiety is covalently coupled to the surface, wherein the silane moiety comprises a targeting moiety having affinity and specificity to the cells or tissues of interest, and wherein the silane moiety comprises a polyalkylene oxide moiety intermediate the core and the targeting agent; and (b) measuring the level of binding of the nanoparticle, wherein an elevated level of binding, relative to normal cells or tissues, is indicative of binding to the cells or tissues of interest.

In one embodiment, the methods for treating a tissue using the nanoparticles is provided. The method includes contacting a tissue of interest with a nanoparticle having affinity and specificity for the tissue of interest, wherein the nanoparticle comprises:

(a) a core comprising a magnetic material and having a surface, and (b) a plurality of silane moieties, wherein each silane moiety is covalently coupled to the surface, wherein at least a portion of the plurality of silane moieties comprise a targeting moiety having affinity and specificity to the tissue of interest, wherein at least a portion of the plurality of silane moieties comprise a therapeutic agent, wherein each silane moiety comprising a targeting agent comprises a polyalkylene oxide moiety intermediate the core and the targeting agent; and wherein each silane moiety comprising a therapeutic agent comprises a polyalkylene oxide moiety intermediate the core and the therapeutic agent.

As noted above, the present invention provides a novel, inexpensive bifunctional trifluoroethylester (TFEE) PEG silane that has low molecular weight and can easily self-assemble on metal oxide-based nanoparticles. This nanoparticle-PEG silane system has the following advantages:

(1) the TFEE PEG has low molecular weight and is especially suitable for cell targeting where the nanoscale dimensions must be enforced;

(2) the TFEE PEG silane is capable of conjugating with both amine and carboxylic groups, the two types of functional groups present in many targeting agents for cancer treatment; the TFEE terminal group provides an easily manipulated headgroup capable of amidation via primary amines in organic solutions or that is hydrolyzed following self-assembly in aqueous conditions; and the formation of the TFEE end group provides a stable leaving group capable of undergoing smooth amidation through the addition of a primary amine;

(3) the 3-aminopropyltriethoxysilane (APS) coupled with the PEG chains confers the stability of PEG self-assembled monolayers (SAMs) and increases PEG packing density on nanoparticles by establishing hydrogen bonding between PEG interchains; and (4) the nanoparticles modified with TFEE silane are well dispersed, which is an essential requirement for in vivo applications to ensure the nanoparticles have the desired targeting functionality, biocompatibility, and long blood circulation time.

To demonstrate the effectiveness of ligand immobilization, folic acid (FA), a widely used targeting agent containing primary amines and carboxylic acid groups native to the structure, was chosen as a representative targeting agent. Folic acid is a low molecular targeting agent whose corresponding receptor is overexpressed on many types of cancer cells. The structure of FA allows conjugation through the TFEE group of the PEG terminus and primary amine on the FA, or the TFEE terminal group can be converted to a primary amine through the addition of ethylenediamine (EDA), which can then be reacted with the carboxyl groups present on the FA. The short chain of folic acid molecules also allows the efficient internalization of nanoparticles by target cells, in contrast to the widely used antibodies that are bulky and thus have difficulty crossing the cell membrane.

Surface modification of metal oxide nanoparticles is critical to ensure the biocompatibility of the nanoparticles both in vitro and in vivo. The present invention provides a functionalized PEG silane capable of ligand immobilization to nanoparticle surfaces. The uptake of superparamagnetic nanoparticles by human breast cancer cells was increased through surface modification with PEG has been demonstrated. See Zhang et al., *Biomaterials* 2002, 23, 1553-1561. The increase in particle uptake was believed to be due to the high solubility of PEG in both polar and nonpolar solvents and thus the increased solubility in the cellular membrane.

Figure 3:
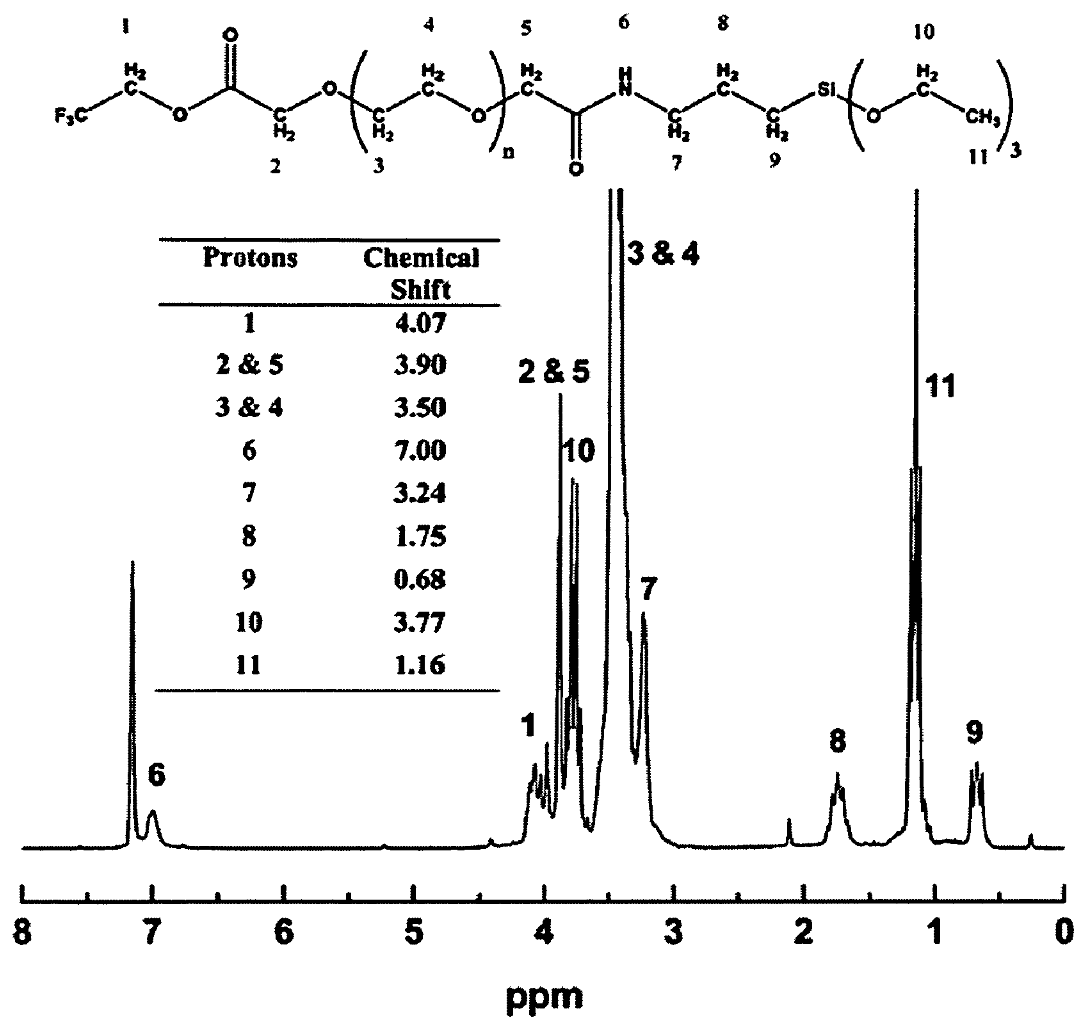
FIG. 3 is the $^1H$ NMR spectrum of the TFEE-terminal PEG silane illustrated in FIG. 1.

A representative PEG silane of the invention was synthesized by the following method and as described in Example 2. A PEG diacid was first converted to an acid chloride that was converted into a bistrifluoroethylester (TFEE), as shown in FIG. 1. By using 3-aminopropyltriethoxy silane (APS), a PEG silane was formed having increased molecular stability through hydrogen bonding between carbonyl and amine groups across the particle surface. The structure of the TFEE terminal PEG silane was identified by $^1$H NMR analysis. The chemical shifts for protons from position 1 to 11 in the TEFE terminal PEG silane are shown in FIG. 3 and its inset table. The molecular structure of the TFEE-terminal PEG silane was confirmed by the presence of all characteristic peaks and peak integration.

Figure 4:
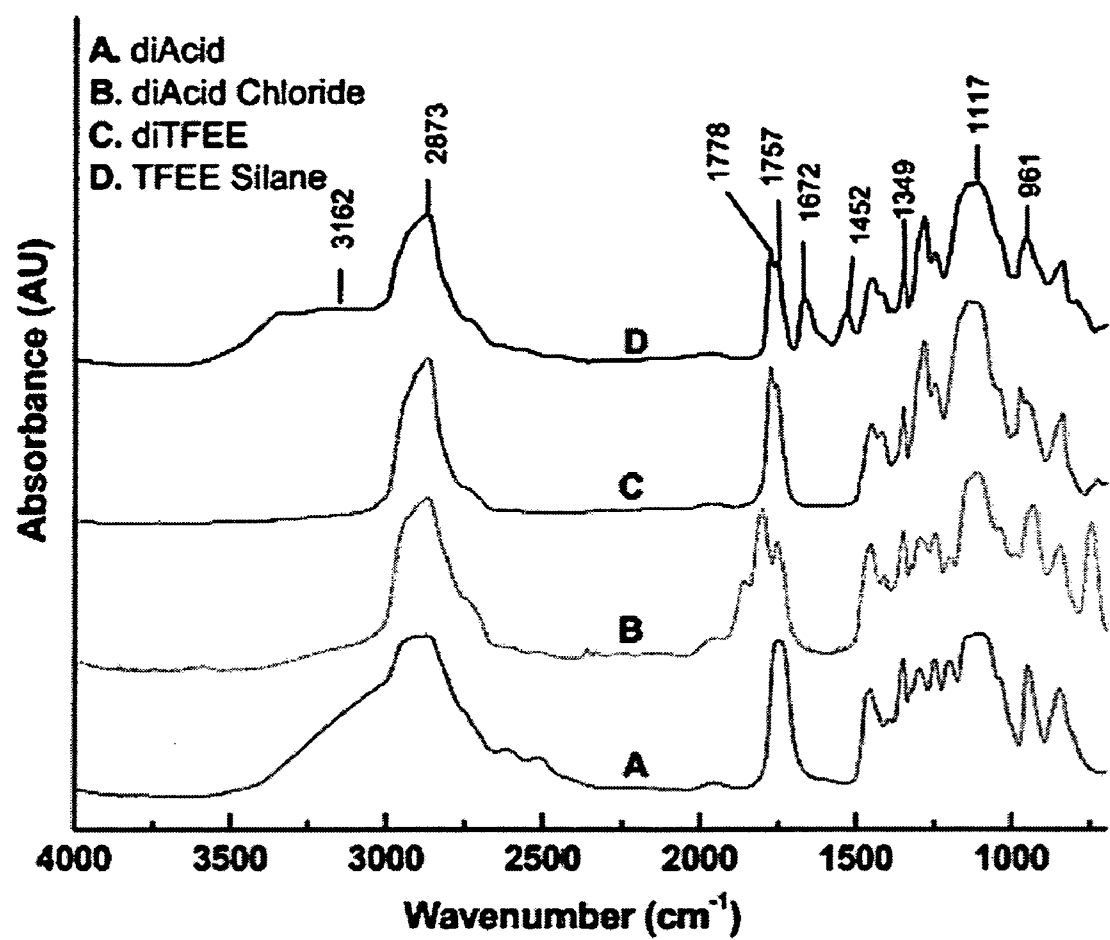
FIG. 4 illustrates the FTIR spectra of (A) PEG-bisdiacid, (B) PEG-acid chloride, (C) PEG-trifluoroethylester, and (D) PEG-trifluoroethylester terminal-silane.

To further verify the successful synthesis of the TFEE terminal PEG silane, FTIR spectra were also collected at each step of the synthesis, as shown in FIG. 4. The broad band at 3200 cm$^{-1}$ corresponds to —OH groups in the dicarboxylic acid structure (A) and was lost following the conversion of PEG diacid to the acid chloride (B), and, as expected, the carbonyl stretch is shifted to higher frequency (above 1800 cm$^{-1}$) and showed greater complexity as a result of substitution of the —OH group with the chlorine group. Conversion of diacid chloride to bis-TFEE (C) collapses the carbonyl band to a simpler structure at about 1760 cm$^{-1}$, typical of an electron-deficient ester carbonyl. The wide —OH stretch band above 3000 cm$^{-1}$ in the PEG diacid is absent in both the acid chloride and the TFEE spectra. Evidence for the half-amide/ester structure (D) is found in the final FTIR spectrum in which both the TFEE ester and the amide carbonyl peaks are clearly seen (1778 and 1672 cm$^{-1}$, respectively). Identification of the TFEE end groups on the molecule was unreliable due to the peak overlap between the PEG ether groups and the C—F stretch groups. The broad band at 3162 cm$^{-1}$ resulted from the —NH stretch band in the amide linkage between the silane and the PEG (D).

Figure 2:
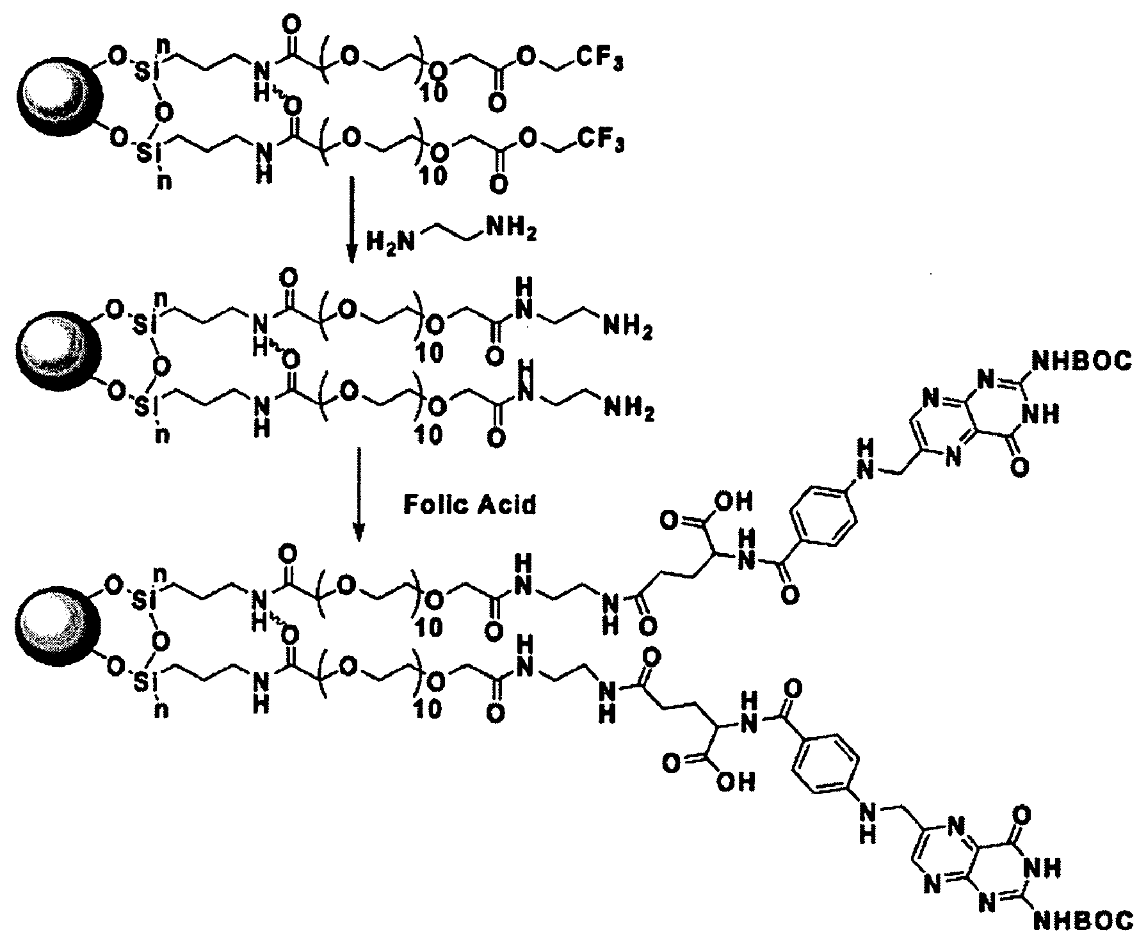
FIG. 2 is a schematic illustration of the immobilization of PEG-amine-FABOC on magnetite nanoparticles to provide reprehensive particles of the present invention.
Figure 5:
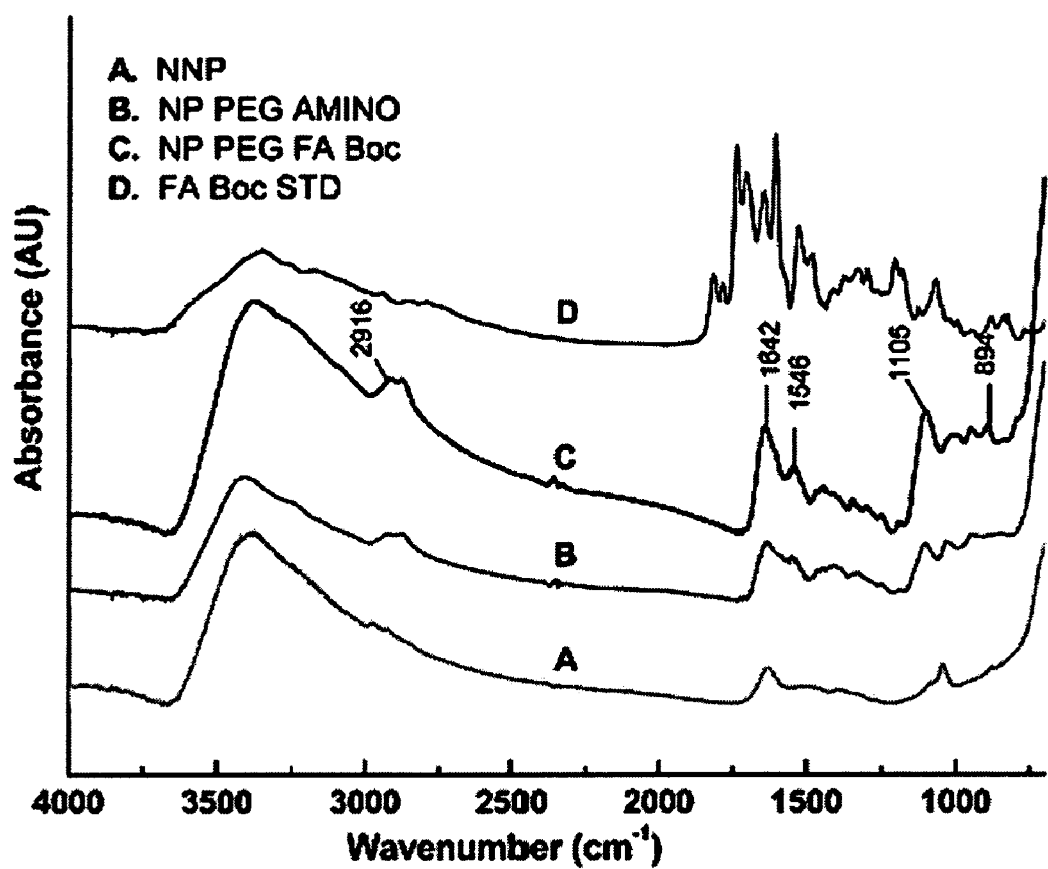
FIG. 5 illustrates the surface modification of nanoparticles with folic acid (FA) through the carboxylic acid groups by FTIR: (A) native (uncoated) nanoparticles, (B) nanoparticles immobilized with PEG-carboxyl terminal SAM, (C) t-Boc-FA grafted nanoparticles, and (D) pure t-Boc-FA-NHS.

Once the synthesis of the TFEE terminal PEG silane had been confirmed with $^1$H NMR and FTIR spectroscopy, the PEG terminal TFEE silane was immobilized on the nanoparticles following the scheme outlined in FIG. 2. To demonstrate the functionality of the newly synthesized TFEE terminal PEG silane, the TFEE end group was converted to a primary amine, allowing t-Boc-protected FA to be immobilized on the primary amine via the two carboxylic acid groups present on the glutamic acid residue. FTIR spectra confirmed the successful surface modification as shown in FIG. 5. The —$CH_2$ stretching vibrations present on native nanoparticles (A) are seen to increase in intensity following the attachment of the PEG-based SAM onto the nanoparticle (B). Following the FA-t-Boc immobilization, the amide carbonyl bands at 1642 and 1546 cm$^{-1}$ were intensified (C).

Figure 6:
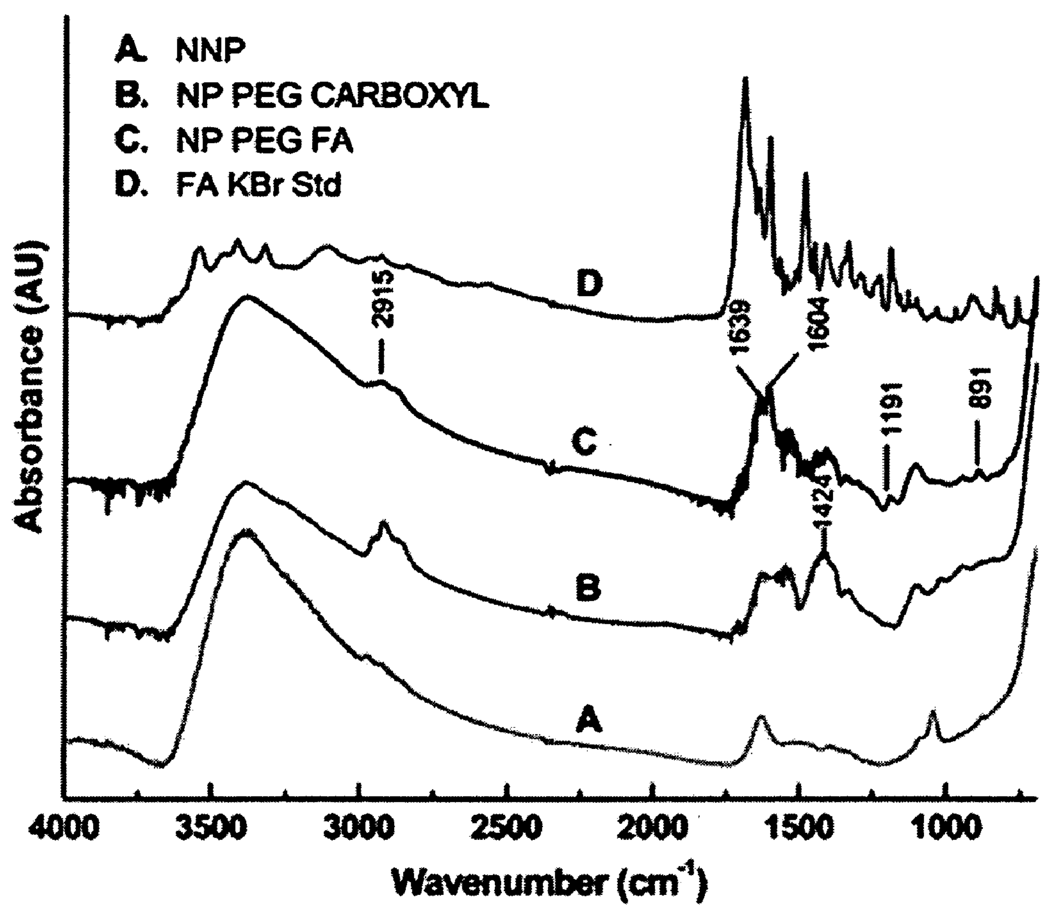
FIG. 6 illustrates the surface modification of nanoparticles with FA via amine groups on the pteridine ring by FTIR: (A) native (uncoated) nanoparticles, (B) nanoparticles immobilized with PEG-carboxyl terminal SAM, (C) FA grafted nanoparticles, and (D) pure FA.

To further demonstrate the conjugating flexibility of the TFEE terminal PEG silane, FA was grafted onto the PEG chain terminus through amidation between the TFEE end group and primary amine groups present on the pteridine rings of FA. The TFEE chain termini are capable of reacting with primary amines in organic solvents and aqueous solvents through either the conversion of the TFEE to a primary amine or the hydrolysis of the TFEE terminal group to the corresponding carboxylic acid in water. The free carboxylic acid was then esterified to a succinimidal ester allowing aqueous amidation of FA. FTIR analysis of the aqueous amidation of FA is shown in FIG. 6. Following the surface modification with the PEG silane, the —$CH_2$ stretching vibrations at 2900 cm$^{-1}$ increased in absorbance, indicating the presence of the PEG silane on the particle surface (B). The broad peak between 1500 and 1600 cm$^{-1}$ in the spectrum is consistent with the carboxylate intermediate. Following FA immobilization, the primary amide peaks increased in absorbance at 1639 and 1604 $cm^{-1}$ (C), consistent with the bonding of the FA molecule to the PEG SAM terminus.

Figure 7:
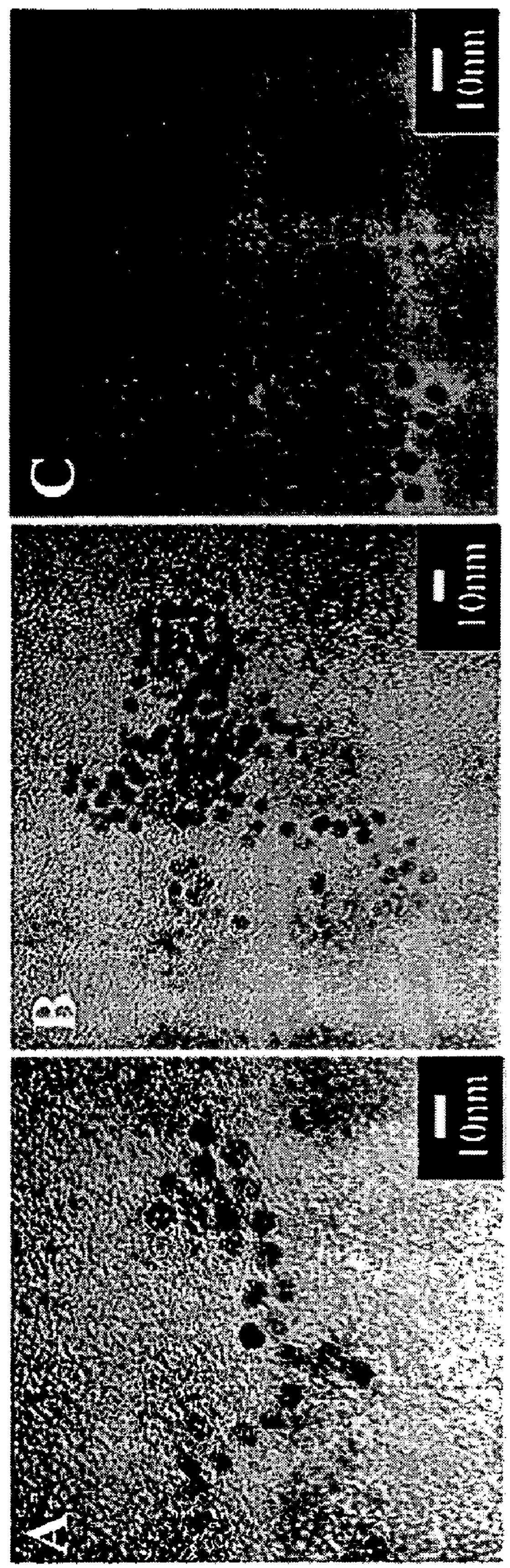
FIG. 7 illustrates TEM micrographs of nanoparticles modified with (A) TFEE terminal PEG silane, (B) amine-terminated PEG, and (C) FA-t-BOC-terminal PEG silane.

TEM images were taken to characterize the dispersivity of nanoparticles before and after surface modification. The addition of APS to the bistrifluoroethylester PEG shown at step D in FIG. 1 was statistical, which might lead to the formation of three types of PEG products: (1) PEG molecules in solution that have not reacted with APS, (2) PEG molecules in solution whose ends have reacted with APS (bis-APS), and (3) bifunctional PEG molecules with both APS and TFEE end groups. Residual PEG bistrifluoroethylester molecules in solution will not react with the nanoparticle during the surface modification due to the lack of amine groups on the nanoparticle surface. The TEM image in FIG. 7A shows that nanoparticles modified with TFEE terminal PEG are well dispersed. This result suggests that the bifunctional PEG molecules were the dominant product during the process of the addition of APS to the bistrifluoroethylester PEG. This is because if the bis-APS PEG silanes were a dominant product, nanoparticles modified with bis-APS silanes may crosslink other nanoparticles and form nanoparticle agglomerates. The TEM image in FIG. 7B shows the dispersion of ethylenediamine-modified nanoparticles. Dispersion of amine terminal PEG silane nanoparticles in toluene is reduced due to the reduction of solubility of the nanoparticles with primary amine groups in the nonpolar solvent. However, following amidation, nanoparticle dispersion is maintained. Dispersion following the immobilization of the FA-t-BOC on the amine terminal PEG silane is also confirmed, as shown in FIG. 7C.

Nanoparticle dispersion has been shown to be a function of PEG molecular weight. See Butterworth et al., *Colloids Surf.* 2001, 179, 93-122. Either higher (e.g., greater than about 5000) or lower (e.g., less than about 350) molecular weight would give rise to high particle stability and dispersivity. High molecular weight can provide complete PEG coverage on nanoparticle surfaces through chains laying across the entire nanoparticle surface. Alternately, low molecular weight can improve particle dispersion as a result of higher monolayer packing densities that would increase steric hindrance. In a representative embodiment, a 600 molecular weight PEG polymer capable of high-density grafting was used. Immobilizing a lower molecular weight PEG SAM on the nanoparticle surface also results in more available functional chain termini; more amidation sites to which targeting ligands may be grafted. In addition, APS at the base of the molecule can enhance the stability of SAM on the nanoparticle surface.

The TFEE end group provides a reactive carboxylic acid group capable of amidation through the immobilization of EDA or folic acid on nanoparticles. This reactive, dual-functional end group allows successful immobilization of molecules containing either primary amine or carboxylic acid groups, thus improving the compatibility of the PEG SAM with prospective targeting agents.

The present invention provides a trifluoroethylester-terminal poly(ethylene glycol) (PEG) silane that was self-assembled on iron oxide nanoparticles. The nanoparticle system thus prepared has the flexibility to conjugate with cell targeting agents via either carboxylic or amine terminal groups for a number of biomedical applications, including magnetic resonance imaging (MRI) and controlled drug delivery. The trifluoroethylester silane was synthesized by modifying a PEG diacid to form the corresponding bistrifluoroethylester (TFEE), followed by a reaction with 3-aminopropyltriethoxysilane (APS). The APS coupled with PEG chains confers the stability of PEG self-assembled monolayers (SAMs) and increases the PEG packing density on nanoparticles by establishing hydrogen bonding between the carbonyl and amine groups present within the monolayer structure. The success of the synthesis of the PEG TEFE silane was confirmed with $^{1}$H NMR and Fourier transform infrared spectroscopy (FTIR). The conjugating flexibility of the PEG TEFE was demonstrated with a representative targeting agent, folic acid, that had carboxylic acid groups and amine terminal groups, respectively, and was confirmed by FTIR. TEM analysis showed the well-dispersed nanoparticles before and after they were coated with PEG and folic acid.

The present invention provides a new functional PEG silane that can be self-assembled on metal oxide colloidal systems to conjugate with cell targeting agents that have either carboxylic or amine terminal groups. The system takes advantage of common carboxylate PEGs and 3-aminopropyltriethyoxysilane, which increases the stability of the PEG monolayer on the nanoparticle surface as a result of formation of hydrogen bonding between PEG interchains. Amidation of PEG termini has been demonstrated by immobilizing FA on the termini of the PEG molecule. By immobilizing FA onto the PEG chain termini via either carboxylic acid or amine groups, the flexibility of this PEG silane system has been established for subsequent immobilization of intended targeting agents. Further, trifluoroethylester-PEG silane amidation is compatible with both organic and aqueous solvents. The trifluoroethylester end group provides a stable leaving group for amidation in organic solvents. Aqueous hydrolization to the corresponding carboxylic acid can be converted to a succimidal ester, a stable leaving group for peptide immobilization in aqueous systems. The compatibility of TFEE-PEG silane amidation with aqueous solvent allows simple immobilization of ligand systems compatible with aqueous solvents alone such as proteins. In addition, PEG silanes with different molecules can be made by converting available diol PEGs with different molecular weights to dicarboxylic acids.

Metal oxide nanoparticles are becoming increasingly important in medicine for MRI contrast enhancement and controlled drug delivery. This functional PEG silane allows covalent immobilization of PEG to the nanoparticle surface to increase particle circulation time in blood and particulate dispersion. In addition, this new monolayer is capable of ligand grafting through amidation, allowing targeted uptake of the nanoparticle ligand system into tumors in vivo. The functionality of this monolayer allows virtually any targeting agent to be immobilized to a nanoparticle surface provided it has either a free carboxylic acid or a primary amine capable of amidation.

The following examples are provided for the purpose of illustrating, not limiting, the invention.

EXAMPLES

Example 1

Materials and Instrumentation

Materials.

The following materials were purchased from Sigma-Aldrich and used as received: PEG biscarboxylate ($M_n$ 600), thionyl chloride, trifluoroethanol, ethylenediamine, 3-aminopropyltriethoxysilane (APS), N-hydroxysuccinimide 97% (NHS), 1-ethyl-3-(3-(dimethylamino)-propyl) carbodiimide (EDAC), iron(III) acetylacetonate, diphenyl ether, oleylamine, oleic acid, folic acid, and tertiarybutoxycarbonyl.

Benzene-$d_6$ was purchased from Cambridge Isotopes. All other solvents were purchased from Fisher Scientific (Hampton, N.H.) or Aldrich (Milwaukee, Wis.

Instrumentation.

$^1$H NMR spectra were acquired with Varian 300 MHz NMR and Bruker DPX-200 NMR spectrometers equipped with a Spectrospin 4.7 T superconducting magnet.

FTIR spectra were acquired using a Nicolet 5-DXB FTIR spectrometer with a resolution of 4 $cm^{-1}$. PEG-silane samples for FTIR analysis were prepared by placing a drop of the liquid between two KBr windows. To analyze the FA immobilized nanoparticles, 2 mg of dried powder of nanoparticle conjugates was mixed with 200 mg of KBr and pressed into a pellet for analysis. TEM images were acquired with a Phillips 400TEM operating at 100 kV. Grids were prepared by dipping 300 mesh silicon-monoxide support films in the PEG-silane immobilized nanoparticle suspensions in water. The grids were then dried under vacuum for 2 h prior to analysis.

Example 2

The Synthesis of a Representative PEG Silane

In this example, the synthesis of a representative PEG silane of the invention is described. The process and products for each reaction step are shown schematically in FIG. 1.

In a round-bottom flask, 100 g (0.167 mol) of PEG biscarboxylate was degassed under a 2-Torr vacuum to remove residual water and air in the liquid. Following degassing, 35 mL (0.48 mol) of thionyl chloride was added dropwise to the neat PEG, converting it to the corresponding diacid chloride. Initially, vigorous bubbling was observed followed by slow bubbling resulted from HCl and $SO_2$ gas. The sample was heated for 1.5 h under nitrogen followed by degassing under a 2-Torr vacuum to remove $SO_2$ gas and excess thionyl chloride. The crude diacid chloride displayed the following $^1$H NMR spectrum: ($C_6D_6$) δ4.08 (brm, 4H, $ClOCCH_2$—), 3.4 (brm, 43H, —$CH_2CH_2$0—).

Next, 32 mL (0.44 mol) of 2,2,2-trifluoroethanol was added dropwise to the PEG diacid chloride under nitrogen. The solution was stirred for 2 h and heated to reflux for 3 h. After being cooled to room temperature, the resulting mixture was placed under a 2-Torr vacuum to remove residual trifluoroethanol from the product. The crude bis-TFEE displayed the following $^1$H NMR spectrum: ($C_6D_6$) δ4.1 (brm, 4H, $CF_3CH_2$—), 3.88 (s, 4H, —$COCH_2$—), 33.42 (brm, 42H, —$CH_2CH_2O$—).

To prepare the PEG silane, 20 g of PEG-ditrifluoroethylester was dissolved in 200 mL of dry toluene. The solution was heated to reflux under nitrogen utilizing a Dean-Stark apparatus to remove residual water from the solution. When the resultant solution cooled to room temperature, 6.4 mL (27 mmol) of APS was added dropwise to the PEG-ditrifluoroethylester solution under nitrogen. The resultant solution was stirred overnight under nitrogen at ambient temperature. Following the amidation reaction, the solvent was removed by distillation. After the distillation, a 0.2 Torr vacuum was applied to remove residual toluene and APS from the PEG silane. The crude half amide-ester displayed the following $^1$H NMR spectrum: ($C_6D_6$) δ7.2 (s, 1H, —$CONHCH_2$—), 4.1 (brm, 4H, $CF_3CH_2$—), 3.9 (s, 3H, —$COCH_2$—), 3.77 (quart., 6H, —$SiOCH_2CH_3$—, J=7.0 Hz), 3.5 (brm, 42H, —$CH_2CH_2O$—), 3.24 (brm, 2H, —$NHCH_2CH_2$—), 1.75 (brm, 2H, —$NHCH_2CH_2CH_2$—, J=7.6 Hz), 1.16 (trip, 9H, —$OCH_2CH_3$, J=7.0 Hz), 0.68 (trip, 6H, —$CH_2CH_2Si$—, J=8.6 Hz).

Example 3

The Synthesis of Representative Superparamagnetic Nanoparticles

In this example, the synthesis of representative superparamagnetic nanoparticles of the invention is described.

Preparation of Oleyl Nanoparticles.

Oleyl-nanoparticles were prepared following the method by Sun with modifications. See Sun et al., *J Am. Chem. Soc.* 2002, 124, 8204-8205, incorporated herein by reference in its entirety.

First, 20 mL of phenyl ether, 0.728 g of iron (III) acetylacetonate, 2.858 g of 1,2-hexadecanediol, 2.11 mL of oleic acid (0.262 M), and 2.75 mL of oleylamine (0.198 M) were mixed in a sonicated bath. The mixture was slowly heated to 265° C. and refluxed under nitrogen for 30 min. During this process, the initial reddish-orange color of the solution gradually changed to dark black, indicative of formation of the oleyl-magnetite nanoparticles. The resultant solution was cooled to room temperature, and 250 mL ethanol was added to yield a black precipitate. The precipitate was collected from the solution with a rare earth magnet and redispersed in 50 mL of hexane to yield a clear homogeneous solution. The suspension was then precipitated with addition of 1 mL of oleic acid, 1 mL of oleylamine, and 250 mL of ethanol. To remove the oleic acid and oleylamine from the nanoparticle surface, the particles were washed in a solution of 1 M ammonium hydroxide in 1-butanol in a sonicating bath followed by washing with toluene, acetone, and ethanol.

Preparation of t-Boc-Protected Folic Acid.

The t-Boc-protected folic acid was prepared by dissolving 9.25 mmol of FA in dimethyl sulfoxide (DMSO). Next, 44 mmol of di-tert-butyl dicarbonate (t-Boc) was added dropwise to the mixture and stirred for 2 h. Following the installation of the t-Boc protecting group, 94 mmol of N-ethyl-N'-(3-dimethylaminopropyl)-carbodiimide hydrochloride (EDAC) and 18.6 mmol of N-hydroxysuccinimide (NHS) were dissolved in 200 mL of DMSO, and the mixture was stirred overnight. The t-Boc-protected FA solution was then added into the NHS/EDAC solution to produce the succinimidal ester on the carboxyl terminus of the FA. The derivatized FA was precipitated in methylene chloride and separated by centrifugation. The product was then freeze-dried to remove the solvent.

PEG SAM Immobilization.

FIG. 2 shows the chemical scheme of modifying nanoparticles with TFEE silane and subsequently conjugating ethylenediamine with carboxylic acid end groups of derivatized folic acid.

First, 200 mg of nanoparticles, prepared as described above, was dispersed in 100 mL of toluene in a round-bottom flask by 20 min of sonication. Following dispersion, 1 mL of the PEG-trifluoroethylester silane, prepared as described in Example 2, was added to the nanoparticle suspension, and the mixture was sonicated for 4 h at 50° C. The resultant PEG-immobilized nanoparticle precipitate was isolated by centrifugation and washed three times with dry toluene to remove residual PEG-silane. The primary amine was created on the immobilized PEG chain termini by flooding the nanoparticle suspension with excess ethylenediamine (EDA). Next, 1 mL of EDA was added to the PEG immobilized nanoparticle suspension and allowed to react for 2 h. The particles were then isolated with a rare earth magnet and washed three times with deionized (DI) water.

Amidation of PEG Chain Termini with Folic Acid.

The primary amine on the SAM terminus of the nanoparticles was amidated with the t-Boc-protected FA by suspending 200 mg of nanoparticles in 50 mL of DMSO along with 75 mg of t-Boc-protected FA. The suspension was sonicated at 60° C. for 2 h. The particles were isolated and washed twice with DMSO and three times with DI water. The particles were then resuspended in 15 mL of DI water.

To produce the carboxylic acid end groups on the PEG SAM termini, the functionalized nanoparticles were washed twice with DI water and stored overnight in DI water to hydrolyze the trifluoroethylester end group. The particles were then resuspended in 50 mL of DI water along with 88 mg of NHS and 750 mg of EDAC to produce a succinimidal ester on the termini of the PEG. The solution was sonicated for 4 h, following which the particles were isolated and resuspended in 50 mL of DMSO along with 75 mg of folic acid. The suspension was stirred for 2 h, allowing the folic acid to react fully with the PEG chain succinimidal ester terminus. The particles were then isolated, washed twice with DMSO and three times with DI water, and stored in DI water.

While illustrative embodiments have been illustrated and described, it will be appreciated that various changes can be made therein without departing from the spirit and scope of the invention.

The invention claimed is:

1. A nanoparticle, comprising:

(a) a core comprising a magnetic material and having a surface; and (b) a plurality of silane moieties, wherein each silane moiety is covalently coupled to the surface, wherein at least a portion of the plurality of silane moieties comprises a targeting agent, and wherein the plurality of silane moieties comprising the targeting agent have the formula:

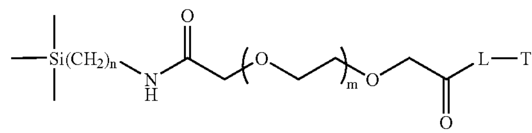

wherein, n is 1, 2, 3, 4, 5, or 6;

m is an integer from about 10 to about 1000;

L is a direct bond or a linker; and

T is the targeting agent.

2. The nanoparticle of claim 1, wherein at least a portion of the plurality of silane moieties comprise a therapeutic agent.

3. The nanoparticle of claim 1, wherein at least a portion of the plurality of silane moieties comprise a fluorescent agent.

4. The nanoparticle of claim 1, wherein at least a portion of the plurality of silane moieties comprise a radiolabel.

5. The nanoparticle of claim 1, wherein the targeting agent is selected from the group consisting of a peptide, a protein, and a nucleic acid.

6. A composition, comprising a nanoparticle of claim 1 suitable for administration to a human subject.

7. A method for detecting cells or tissues by magnetic resonance imaging, comprising:

(a) contacting cells or tissues of interest with a nanoparticle having affinity and specificity for the cells or tissues of interest, wherein the nanoparticle comprises (i) a core comprising a magnetic material and having a surface, and (ii) a plurality of silane moieties, wherein each silane moiety is covalently coupled to the surface, wherein at least a portion of the plurality of silane moieties comprises a targeting agent having affinity and specificity to the cells or tissues of interest, and wherein the plurality of silane moieties comprising the targeting agent have the formula:

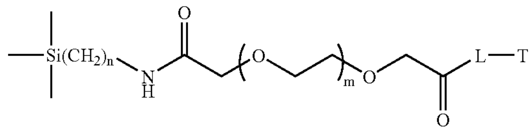

wherein, n is 1, 2, 3, 4, 5, or 6, m is an integer from about 10 to about 1000,

L is a direct bond or a linker, and

T is the targeting agent; and (b) measuring the level of binding of the nanoparticle, wherein an elevated level of binding, relative to normal cells or tissues, is indicative of binding to the cells or tissues of interest.

* * * * *